(12) United States Patent
Barral et al.

(10) Patent No.: US 10,105,474 B2
(45) Date of Patent: Oct. 23, 2018

(54) SYNCHRONIZING BREAST PUMPING WITH INFANT FEEDING

(71) Applicant: EXPLORAMED NC7, INC., Mountain View, CA (US)

(72) Inventors: Joelle Barral, Mountain View, CA (US); Venita Chandra, Belmont, CA (US); Mary Garrett, Redwood City, CA (US); Jessica Hudak, Washington, DC (US); Asha Nayak, Sunnyvale, CA (US); Erika Palmer, Broomfield, CO (US); Sandra Waugh Ruggles, Sunnyvale, CA (US); Beverly Tang, Palo Alto, CA (US)

(73) Assignee: ExploraMed NC7, Inc., Mountain View, CA (US)

( * ) Notice: Subject to any disclaimer, the term of this patent is extended or adjusted under 35 U.S.C. 154(b) by 94 days.

(21) Appl. No.: 15/417,343

(22) Filed: Jan. 27, 2017

(65) Prior Publication Data
US 2017/0136160 A1 May 18, 2017

Related U.S. Application Data

(63) Continuation of application No. PCT/US2015/044521, filed on Aug. 10, 2015.
(Continued)

(51) Int. Cl.
*A61M 1/06* (2006.01)
*A61M 31/00* (2006.01)
*A61B 5/00* (2006.01)

(52) U.S. Cl.
CPC ............. *A61M 1/062* (2014.02); *A61B 5/486* (2013.01); *A61B 5/4857* (2013.01); *A61M 1/06* (2013.01);
(Continued)

(58) Field of Classification Search
CPC .................. A61M 1/062; A61M 1/06; A61M 2205/3389; A61M 2209/088; A61B 5/4857; A61B 5/486; A61B 5/4288
See application file for complete search history.

(56) References Cited

U.S. PATENT DOCUMENTS 4,263,912 A    4/1981 Adams
5,542,921 A    8/1996 Meyers et al.
(Continued)

FOREIGN PATENT DOCUMENTS

CN    2628060 Y     7/2004
CN    201353322    12/2009
(Continued)

OTHER PUBLICATIONS

Chiu et a., Development of a piezoelectric polyvinylidene fluoride (PVDF) polymer based sensor patch for simultaneous heartbeat and respiration monitoring, Sensors and Actuators A: Physical, vol. 189, Jan. 15, 2013, pp. 328-334.
(Continued)

*Primary Examiner* — Rebecca E Eisenberg

(57) ABSTRACT

A system for synchronizing one or more breast-pumping sessions of an individual (such as a mother) and milk consumption by a second individual (such as a baby or infant) is described. In particular, based on measurements of a volume of the collected milk as a function of time and received information specifying milk consumption by the second individual as a function of time, a control circuit may determine a need for milk. Then, the control circuit may provide feedback based on the determined need for milk that synchronizes the one or more breast-pumping sessions and the milk consumption. For example, the feedback may alert
(Continued)

the individual to initiate a breast-pumping session and/or may provide a signal to a breast pump that initiates a breast-pumping session.

8 Claims, 11 Drawing Sheets

Related U.S. Application Data

(60) Provisional application No. 62/060,264, filed on Oct. 6, 2014, provisional application No. 62/036,052, filed on Aug. 11, 2014.

(52) U.S. Cl.
CPC ............ *A61M 2205/3389* (2013.01); *A61M 2205/3523* (2013.01); *A61M 2205/3561* (2013.01); *A61M 2205/3592* (2013.01); *A61M 2205/36* (2013.01); *A61M 2205/502* (2013.01); *A61M 2209/088* (2013.01)

(56) References Cited

U.S. PATENT DOCUMENTS

| | | | |
|---|---|---|---|
| 5,634,468 A | 6/1997 | Platt et al. | |
| 5,827,191 A | 10/1998 | Rosenfeld | |
| 5,902,267 A | 5/1999 | Medo | |
| 6,033,367 A | 3/2000 | Goldfield | |
| 6,045,529 A | 4/2000 | Nuesch | |
| 6,264,049 B1 | 7/2001 | Shteynberg | |
| 6,273,868 B1 | 8/2001 | Nordvik | |
| 6,287,252 B1 | 9/2001 | Lugo | |
| 6,328,082 B1 | 12/2001 | Lafond | |
| 6,379,327 B2 | 4/2002 | Lundy | |
| 6,440,100 B1 | 8/2002 | Prentiss | |
| 6,547,756 B1 | 4/2003 | Greter et al. | |
| 6,712,785 B2 | 3/2004 | Morton et al. | |
| 7,201,735 B2 | 4/2007 | Atkin et al. | |
| 7,223,255 B2 | 5/2007 | Myers et al. | |
| 7,559,915 B2 | 7/2009 | Dao | |
| D604,503 S | 11/2009 | Patadia | |
| 7,621,797 B1 | 11/2009 | Hershkovich | |
| 7,824,363 B2 | 11/2010 | Myers | |
| 7,835,230 B1 | 11/2010 | Chang | |
| 7,988,661 B2 | 8/2011 | Silver et al. | |
| 8,057,425 B1 | 11/2011 | Myers et al. | |
| 8,070,715 B2 | 12/2011 | Quackenbush et al. | |
| 8,070,716 B2 | 12/2011 | Sutrina et al. | |
| 8,118,772 B2 | 2/2012 | Dao | |
| 8,262,606 B2 | 9/2012 | Greter et al. | |
| 8,282,596 B2 | 10/2012 | Greter et al. | |
| 8,353,865 B2 | 1/2013 | Thilwind et al. | |
| 8,376,986 B2 | 2/2013 | Van Schijndel et al. | |
| 8,597,234 B2 | 12/2013 | Larsson | |
| 8,671,701 B2 | 3/2014 | McKendry | |
| 8,684,961 B2 | 4/2014 | Gottenbos et al. | |
| 8,801,495 B1 | 8/2014 | Guidon | |
| 8,979,819 B2 | 3/2015 | Sherman | |
| 9,050,404 B2 | 6/2015 | Silver et al. | |
| 9,162,016 B2 | 10/2015 | Geddes | |
| 9,173,587 B2 | 11/2015 | Van Schijndel et al. | |
| 9,199,017 B2 | 12/2015 | Greter | |
| 9,278,167 B2 | 3/2016 | Aalders et al. | |
| 2003/0191433 A1 | 10/2003 | Prentiss | |
| 2004/0122358 A1 | 6/2004 | Kent | |
| 2004/0186788 A1 | 9/2004 | Czuchry | |
| 2005/0059928 A1 | 3/2005 | Larsson | |
| 2005/0234370 A1 | 10/2005 | Beal et al. | |
| 2006/0106334 A1 | 5/2006 | Jordan et al. | |
| 2010/0217148 A1 | 8/2010 | Binder | |
| 2011/0034869 A1 | 2/2011 | Greter | |
| 2011/0036801 A1 | 2/2011 | Martijn | |
| 2011/0071466 A1 | 3/2011 | Silver et al. | |
| 2011/0245763 A1 | 10/2011 | Myers | |
| 2011/0251552 A1 | 10/2011 | Brittner | |
| 2012/0197187 A1 | 8/2012 | LaFave | |
| 2012/0277728 A1 | 11/2012 | Weber et al. | |
| 2013/0023821 A1 | 1/2013 | Khalil et al. | |
| 2013/0123688 A1 | 5/2013 | Bosman et al. | |
| 2013/0131588 A1 | 5/2013 | Silver et al. | |
| 2013/0178793 A1 | 7/2013 | Matias | |
| 2014/0066734 A1 | 3/2014 | Zdeblick | |
| 2014/0142501 A1 | 5/2014 | Clark | |
| 2014/0242213 A1 | 8/2014 | McCarty | |
| 2014/0263611 A1 | 9/2014 | Bauer | |
| 2014/0288466 A1 | 9/2014 | Alvarez | |
| 2014/0311239 A1 | 10/2014 | Marjanovic | |
| 2014/0378895 A1 | 12/2014 | Barack | |
| 2014/0378946 A1 | 12/2014 | Thompson | |
| 2015/0065994 A1 | 3/2015 | Fridman | |
| 2015/0065996 A1 | 3/2015 | Bartlett, II | |
| 2015/0112298 A1 | 4/2015 | Pirzada | |
| 2015/0150761 A1 | 6/2015 | Lanternari | |

FOREIGN PATENT DOCUMENTS

| | | |
|---|---|---|
| CN | 102149415 | 8/2011 |
| CN | 202233080 | 5/2012 |
| EP | 2456482 B1 | 11/2016 |
| GB | 2342446 A | 4/2000 |
| WO | WO2000041745 | 7/2000 |
| WO | WO2001054488 | 8/2001 |
| WO | WO2003028616 | 4/2003 |
| WO | WO2011010255 | 1/2011 |
| WO | WO2011144984 A | 11/2011 |
| WO | WO2013088310 | 6/2013 |
| WO | WO2013166462 | 11/2013 |
| WO | WO2013184004 | 12/2013 |
| WO | WO2013187763 | 12/2013 |
| WO | WO2015120321 | 8/2015 |
| WO | WO2016105718 | 6/2016 |

OTHER PUBLICATIONS

Double Electric Breast Pump/Dr. Brown's, http://www.drbrownsbaby.com/breastfeeding-product/breast-pumps/double-electric, May 15, 2014.

SYNCHRONIZING BREAST PUMPING WITH INFANT FEEDING

CROSS REFERENCE TO RELATED APPLICATION

This application claims priority under 35 U.S.C. § 119(e) to: U.S. Provisional Application Ser. No. 62/036,052, entitled "Breast Pump," by Joelle K. Banal, Venita Chandra, Mary K. Garrett, Asha S. Nayak, Erika I. Palmer, Sandra Waugh Ruggles and Beverly T. Tang, filed on Aug. 11, 2014; and to U.S. Provisional Application Ser. No. 62/060,264, entitled "Systems and Methods for Managing Breast Pumping," by Joelle K. Barral, Venita Chandra, Jessica A. Hudak, Erika I. Palmer, Sandra Waugh Ruggles and Beverly T. Tang, filed on Oct. 6, 2014, the contents of both of which are herein incorporated by reference.

BACKGROUND

Field

The described embodiments relate to an article of clothing that includes a breast pump and techniques for using the breast pump, including synchronizing one or more breast-pumping sessions of a woman with milk consumption by a baby or an infant.

Related Art

Studies indicate that breast milk provides important vitamins and nutrients for babies. However, sometimes direct breastfeeding is not an option or may not desirable.

Breast pumps make it possible for a mother to extract breast milk for her infant(s). In addition, breast pumps can help a mother continue lactating at regular intervals so that she does not lose the ability to generate milk during times when she is away from her infant or when a baby may not be nursing. For example, premature infants or babies born with defects may be put in a neonatal intensive care unit (NICU) at a hospital, and therefore may not be able to nurse for a time. In these cases, a breast pump not only keeps a mother lactating, but may allow a baby in a NICU, who is able, to receive breast milk.

However, there are challenges associated with existing breast pumps. In particular, many breast pumps are noisy, and can require regular cleaning and maintenance, which are time-consuming and expensive. Moreover, collecting milk, transferring it to a clean container, and then finding a place to store the milk can be time-consuming and frustrating. In addition, these actions often require a lot of attention or focus, which can be difficult for a mother with a newborn baby. For example, a mother may need to hold a pump or manually pump a device to extract milk. Then, the mother may need to switch breasts and repeat these operations, all while holding and encouraging their child.

Furthermore, existing breast pumps often do not cause sufficient milk letdown, such that mothers may have to wait several minutes or even hours for another milk letdown. This problem may be compounded by the uncertainty it causes, because a mother may not know when her body is going to be ready to produce milk again. In some instances, the mother may have to put away the breast pump only to subsequently have to get it out right away because her milk is coming. The whole process can, therefore, become time-consuming and frustrating.

Hence, there is a need for an improved breast pump and a technique for using a breast pump.

SUMMARY

One group of described embodiments includes an article of clothing. This article of clothing includes a collection mount having an inner surface that mechanically couples to an areola of a breast of an individual, where the collection mount has an opening from the inner surface to an outer surface of the collection mount that is defined by an edge. Moreover, the article of clothing includes a compression element that surrounds at least a portion of the breast, and a pump mechanically coupled to the collection mount by tubing embedded in the article of clothing. During operation, the compression element applies a type of compression pattern at a location on the breast to facilitate lactation. In addition, the pump, in conjunction with the compression element, collects milk. Furthermore, the article of clothing includes a reservoir mechanically coupled to the pump by second tubing embedded in the article of clothing, which stores the collected milk.

For example, during operation the pump may apply a pressure less than atmospheric pressure to a cavity between the areola and the inner surface of the collection mount. In particular, the compression element and the pump may apply time-varying compression to the breast and time-varying suction on the areola to collect the milk. Because of the type of compression pattern concurrently applied by the compression element, a maximum magnitude of the pressure applied by the pump may be less than a pain threshold of the individual. Note that the maximum magnitude of the pressure applied by the pump may be selectable.

In some embodiments, the article of clothing includes: a band that attaches around a circumference of a torso of the individual; and shells, having inner surfaces, which are mechanically coupled to the band. The shells may support breasts of the individual. Moreover, the collection mount and the compression element may be included within a cavity defined by an inner surface of one of the shells. Note that a portion of the tubing may be included in cavities in the one of the shells. Furthermore, the article of clothing may include a cooling element that, during operation, reduces a temperature of the cavities to a temperature below room temperature. Additionally, a stiffness of outer surfaces of the shells may be greater than a stiffness of the internal surfaces of the shells.

Note that the type of compression pattern may include: a circular pattern, a spiral pattern, a rhythmic pattern, a random pattern, a programmable pattern, and/or a localized pattern. Moreover, the type of compression pattern and the location may be selectable.

Furthermore, the compression element may include channels. During operation, the compression element may generate the type of compression pattern using a gas and/or a liquid in the channels. Alternatively or additionally, the compression element may include bearings, and during operation the compression element may generate the type of compression pattern using the bearings.

In some embodiments, during operation, the cooling element reduces a temperature of the reservoir to a temperature below room temperature.

Moreover, the article of clothing may include an interface circuit, electrically coupled to the compression element and the pump, which communicates with an electronic device using wireless communication. During operation, the interface circuit may receive an activation command from the electronic device to turn on the compression element and the pump and/or may subsequently receive a deactivation command from the electronic device to turn off the compression element and the pump.

Furthermore, the article of clothing may include a milk letdown sensor electrically coupled to the compression element and the pump. During operation, the milk letdown sensor may detect when the individual's milk has letdown, and may provide an activation signal to turn on the compression element and the pump. Alternatively or additionally, when the milk letdown sensor detects that the individual's milk has letdown, the milk letdown sensor may provide feedback to the individual.

In some embodiments, the article of clothing includes a feedback device. During operation of the compression element and the pump, the feedback device may provide, to the individual, encouragement and/or feedback about milk collection.

Moreover, the article of clothing may include a lactation sensor. During operation of the compression element and the pump, the lactation sensor may measure: a milk flow rate, and/or a volume of collected milk.

Another embodiment provides a method for collecting milk from the breast using the article of clothing. During operation of the article of clothing, the compression element may compress the location on the breast to facilitate lactation using the type of compression pattern. Moreover, the pump mechanically coupled by tubing to the collection mount may apply suction to the areola of the breast. Next, the reservoir collects the milk based on the compression and the suction.

A second group of described embodiments includes a system. This system includes: a breast pump, a lactation sensor, an interface circuit that communicates with a consumption sensor associated with a bottle, and a control circuit. During operation, the breast pump collects milk from an individual during one or more breast-pumping sessions. Moreover, the lactation sensor measures a volume of the collected milk as a function of time. Furthermore, the interface circuit receives information specifying milk consumption by a second individual (such as a baby) as a function of time. Additionally, the control circuit determines a need for milk based on a temporal pattern of the volume of the collected milk and a temporal pattern of the milk consumption, and provides feedback based on the determined need for milk that synchronizes the one or more breast-pumping sessions and the milk consumption.

Note that the feedback may alert the individual to initiate a breast-pumping session. Alternatively or additionally, the feedback may include a signal to the breast pump that initiates a breast-pumping session.

Moreover, the system may include a sensor. During operation, the sensor may measure: a vital sign of the individual as a function of time, a biomarker of the individual as a function of time, and/or an activity pattern of the individual as a function of time. Alternatively or additionally, the vital-sign measurements, a biomarker of the individual as a function of time, and/or the activity pattern may be received by the interface circuit. Then, the control circuit may determine the need for milk based on: a temporal pattern of the vital sign, a temporal pattern of the biomarker, and/or a temporal pattern of the activity pattern.

Furthermore, the interface circuit may receive additional information specifying: a vital sign of the second individual as a function of time, a biomarker of the second individual as a function of time, and/or an activity pattern of the second individual as a function of time. Then, the control circuit may determine the need for milk based on: a temporal pattern of the vital sign of the second individual, a temporal pattern of the biomarker of the second individual, and/or a temporal pattern of the activity pattern of the second individual.

In some embodiments, the control circuit determines the need for milk based on a day of the week (and, more generally, a timestamp).

Note that the received information may specify: a temperature of milk in the bottle, and/or a time duration since the milk in the bottle was collected. The control circuit may determine the need for milk based on: the temperature of the milk in the bottle, and/or the time duration.

Moreover, the system may include memory that stores a program module with instructions for determining the need for milk and providing the feedback, and the control circuit may include a processor. During operation, the processor may execute the program module.

Furthermore, the determining may be based on a supervised-learning model that relates the need for milk, the temporal pattern of the volume of the collected milk, and the temporal pattern of the milk consumption.

Note that the feedback may maximize an average volume of the milk collected during a given breast-pumping session.

Additionally, the system may include a feedback device. During a given breast-pumping session, the feedback device may provide, to the individual, encouragement about milk collection.

Another embodiment provides a computer-program product for use with the A/V hub. This computer-program product includes instructions for at least some of the operations performed by the system.

Another embodiment provides a method for synchronizing the one or more breast-pumping sessions of the individual and milk consumption by the second individual. This method includes at least some of the operations performed by the system.

This Summary is provided merely for purposes of illustrating some exemplary embodiments, so as to provide a basic understanding of some aspects of the subject matter described herein. Accordingly, it will be appreciated that the above-described features are merely examples and should not be construed to narrow the scope or spirit of the subject matter described herein in any way. Other features, aspects, and advantages of the subject matter described herein will become apparent from the following Detailed Description, Figures, and Claims.

BRIEF DESCRIPTION OF THE FIGURES

Note that like reference numerals refer to corresponding parts throughout the drawings. Moreover, multiple instances of the same part are designated by a common prefix separated from an instance number by a dash.

DETAILED DESCRIPTION

One group of embodiments provides an article of clothing with an embedded breast pump. This breast pump combines a type of compression pattern at a location on a woman's breast with suction or vacuum to the areola or a region proximate to the nipple provided by a pump to collect milk. For example, the compression element may apply time-varying compression to the breast and the pump may provide time-varying suction on the areola to collect the milk. However, because the type of compression pattern is concurrently applied with the suction, the pressure applied by the pump may be reduced. In addition, to making mechanical breast feeding more comfortable, the pump may be smaller and less noisy. In conjunction with embedding the breast pump in the article of clothing, these features may allow women to collect milk discretely and at a time and place that is convenient for them (such as while at work).

A second group of embodiments provides a system for synchronizing one or more breast-pumping sessions of an individual (such as a mother) and milk consumption by a second individual (such as a baby or infant). In particular, based on measurements of a volume of the collected milk as a function of time and received information specifying milk consumption by the second individual as a function of time, a control circuit may determine a need for milk. Then, the control circuit may provide feedback based on the determined need for milk that synchronizes the one or more breast-pumping sessions and the milk consumption. For example, the feedback may alert the individual to initiate a breast-pumping session and/or may provide a signal to a breast pump that initiates a breast-pumping session.

By facilitating effective breast pumping, the article of clothing and the system may increase a mother's milk production. In addition, by making breast pumping easier and more discrete, the article of clothing and the system may reduce the time needed and the frustration associated with existing breast pumps, and may improve the user experience of the mother when using the breast pump. Consequently, the article of clothing and the system may encourage breast pumping, thereby allowing mothers to breast feed for a longer time, thereby providing health benefits for babies and infants.

Figure 1:
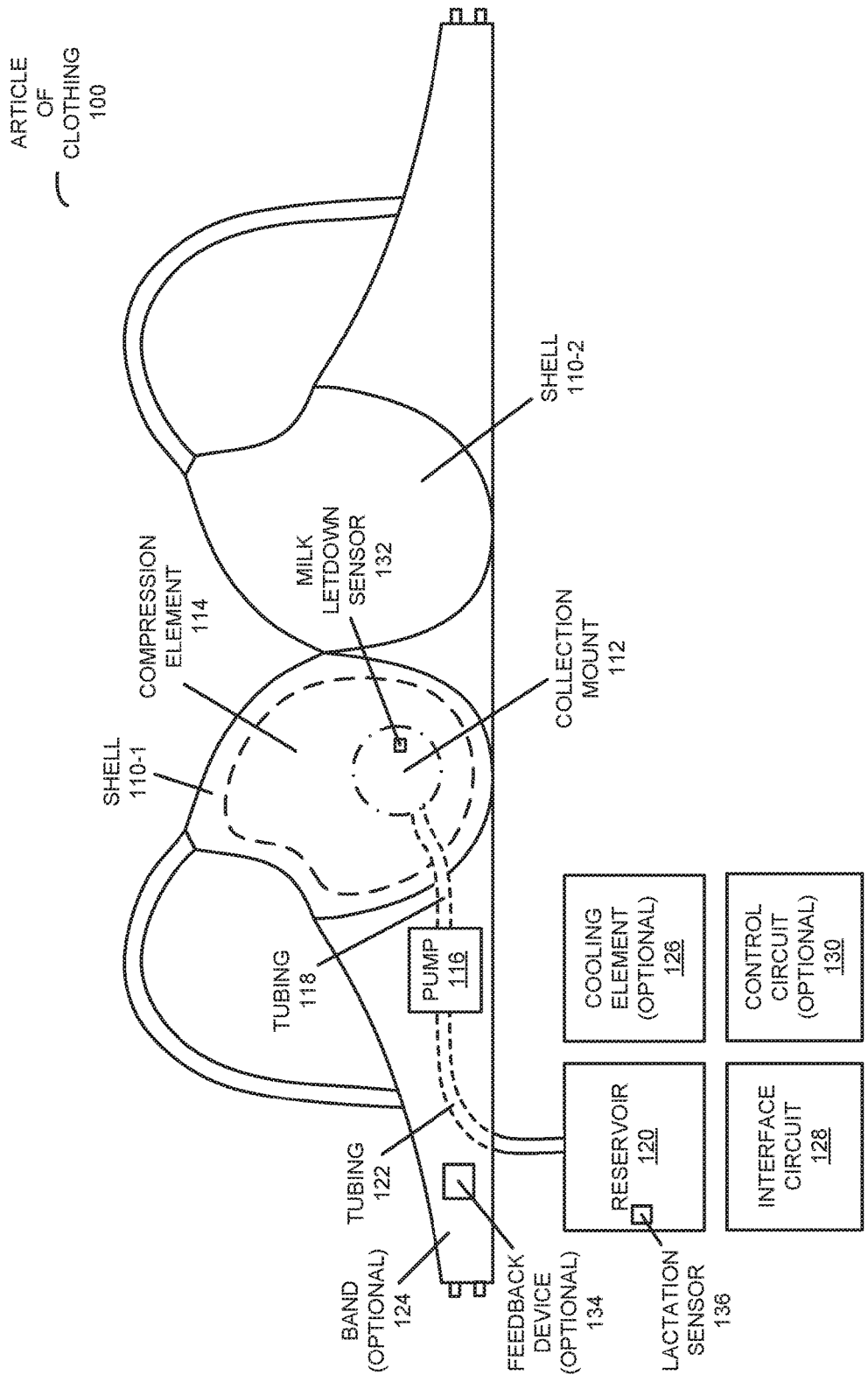
FIG. 1 is a block diagram illustrating an article of clothing in accordance with an embodiment of the present disclosure.
Figure 2:
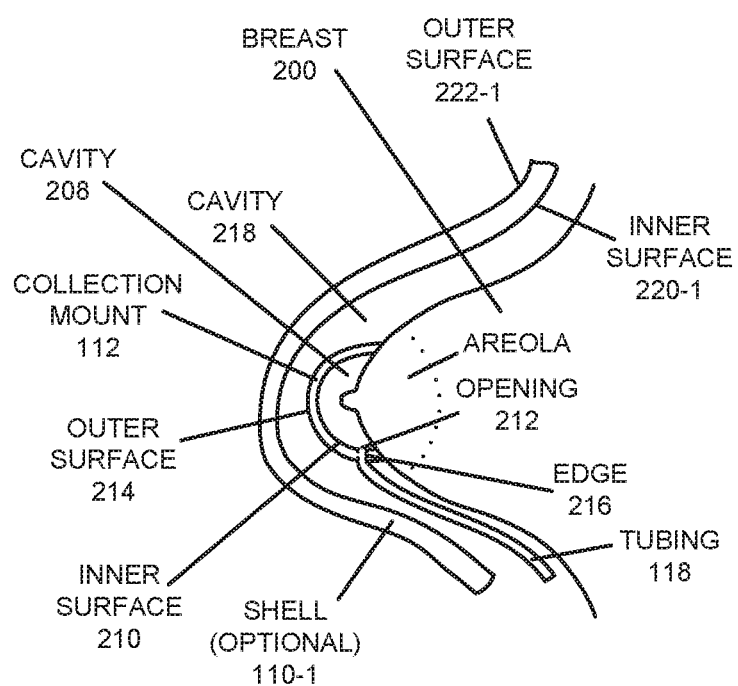
FIG. 2 is a drawing illustrating a side view of a breast and a collection mount in accordance with an embodiment of the present disclosure.

We now describe embodiments of the article of clothing. FIG. 1 presents a block diagram illustrating an article of clothing 100. This article of clothing includes a collection mount 112. As illustrated in FIG. 2, which presents a drawing illustrating a side view of a breast 200, collection mount 112 has an inner surface 210 that mechanically couples to (and makes a seal with) an areola of breast 200 of an individual (such as a mother and, more generally, a woman that is lactating), and collection mount 112 has an opening 212 from inner surface 210 to an outer surface 214 that is defined by an edge 216. For example, collection mount 112 may include: silicone, plastic and/or a composite material.

Referring back to FIG. 1, article of clothing 100 includes a compression element 114 (which is described further below with reference to FIG. 3) that surrounds at least a portion of the breast, and a pump 116 mechanically coupled to collection mount 112 by tubing 118 embedded or included in article of clothing 100. Alternatively, pump 116 may be mechanically coupled to collection mount 112 without using tubing.

During operation, compression element 114 applies a type of compression pattern at one or more locations on the breast to facilitate lactation. In addition, pump 116, in conjunction with compression element 114, collects milk. In particular, the milk may be collected and stored in reservoir 120 in article of clothing 100, which is mechanically coupled to pump 116 by tubing 122 that is included in or embedded in article of clothing 100.

For example, during operation pump 116 may apply a pressure less than atmospheric pressure to a cavity 208 (defined by inner surface 210 and the individual's skin) between the areola and inner surface 210 of collection mount 112 via tubing 118 and opening 212. In particular, compression element 114 and pump 116 may apply time-varying compression to breast 200 (FIG. 2) and time-varying suction on the areola to collect the milk (such as a push-pull arrangement with alternating suction and massage). Because of the type of compression pattern concurrently applied by compression element 114, a maximum magnitude of the pressure applied by pump 116 may be less than that applied by pumps in existing breast pumps, such as a maximum magnitude of the pressure that is less than a pain threshold of the individual. (Thus, pump 116 may include: a roughing pump, an insulin pump, a portable pump, etc.) Furthermore, because of the type of compression pattern concurrently applied by compression element 114, a cyclic suction pattern applied by pump 116 may have a smaller fundamental frequency than that applied by pumps in existing breast pumps or may even be reduced to zero (i.e., no cyclic component), thereby reducing the noise level and enhancing discretion during a pumping session. Note that the maximum magnitude of the pressure applied by pump 116 may be selectable by the individual via a knob or button in a physical control interface (which is sometimes referred to as an input/output or I/O interface). Alternatively, as described further below, the maximum magnitude of the pressure may be remotely selectable using an electronic device (such as a cellular telephone of the individual) via interface circuit 128. In some embodiments, during breast pumping, steady pressure and/or heat from a heating element (not shown) are applied to one or more locations on breast 200 (FIG. 2).

Article of clothing 100 may include a wide variety of types of clothing, such as a shirt, a jacket, a backpack, a vest, an undergarment (such as a corset, a brassiere or another breast-supporting article), etc. In some embodiments, article of clothing 100 includes: an optional band 124 that attaches around a circumference of a torso of the individual; and optional shells 110, which are mechanically coupled to optional band 124. These optional shells may support the breasts of the individual. Moreover, as shown in FIG. 2, collection mount 112 and compression element 114 may be included within a cavity 218 defined by an inner surface (such as inner surface 220-1) of at least one of optional shells 110 (such as optional shell 110-1). Note that a portion of tubing 122 may be included in cavity 218. In some embodiments, pump 116 is held in place by its own straps or another support material (such as body tape or another body adhesive).

Furthermore, article of clothing 100 (FIG. 1) may include an optional cooling element 126 in FIG. 1 (such as a Peltier cooling device) that, during operation, reduces a temperature of cavities 208 and/or 218 to a temperature below room temperature (i.e., that cools cavities 208 and/or 218). In some embodiments, during operation, optional cooling element 126 reduces a temperature of reservoir 120 (FIG. 1) to a temperature below room temperature (i.e., that cools reservoir 120 in FIG. 1).

Additionally, a stiffness of outer surfaces of optional shells 110 (such as outer surface 222-1) may be greater than a stiffness of the internal surfaces of optional shells 110 (such as inner surface 220-1). Thus, optional shells 110 may have a hard exterior (such as a hard plastic, a metal, a composite, etc.) that hides or masks mechanical motion associated with compression element 114 (and, more generally, the breast pumping) and the inner surface may be a softer material (such as a soft plastic, e.g., a thermoplastic, silicone, a fabric, a foam, etc.). In some embodiments, optional shells 110 include breast-soothing elements, such as a gel pad. Alternatively, the outer surfaces of optional shells 110 may be made of a softer, conformable material (such as a thermoplastic or silicone) to mimic the outer shape of a natural breast, while the inner surface of optional shells 110 may be comprised of a hard cavity that holds the breasts in place and contains, hides, or masks the mechanical motion associated with compression element 114 (and, more generally, the breast pumping).

As noted previously, article of clothing 100 may include an interface circuit 128, electrically coupled to compression element 114 and pump 116, which communicates with an electronic device (such as a cellular telephone of the individual) using wireless communication. During operation, interface circuit 128 may receive an activation command from the electronic device to turn on compression element 114 and/or pump 116. Subsequently, interface circuit 128 may receive a deactivation command from the electronic device to turn off compression element 114 and/or pump 116. A description of wireless communication with article of clothing 100 (such as with optional electronic device 616) is described further below with reference to FIG. 6.

Moreover, article of clothing 100 may include a milk letdown sensor 132 electrically coupled to compression element 114 and pump 116. During operation, milk letdown sensor 132 may detect when the individual's milk is ejected or has letdown, and may provide an activation signal to turn on compression element 114 and/or pump 116. (Similarly, when milk ejection or flow has stopped or dropped below a predefined threshold, milk letdown sensor 132 may subsequently provide a deactivation signal to turn off compression element 114 and/or pump 116.) For example, milk letdown sensor 132 may detect the presence of milk below the surface or proximate to the nipple of the breast, such as via an optical or an electrical or conductivity measurement. Alternatively or additionally, when milk letdown sensor 132 detects that the individual's milk has letdown, milk letdown sensor 132 may provide feedback to the individual. For example, article of clothing 100 may include an optional feedback device 134 that provides the feedback (such as a vibration motor, one or more speakers, etc.). In addition, during operation of compression element 114 and/or pump 116, optional feedback device 134 may provide, to the individual, encouragement and/or feedback about milk collection (such as how long the individual has been breast pumping and/or how much milk has been collected).

Furthermore, article of clothing 100 may include a lactation sensor 136. During operation of compression element 114 and/or pump 116, lactation sensor 136 may measure: a milk flow rate, and/or a volume of collected milk (such as the volume in reservoir 120). For example, lactation sensor 136 may include: an optical sensor, a flow sensor, a level sensor, and/or a resistance sensor. Lactation sensor 136 may indicate that reservoir 120 is full and/or that the milk is due to be cooled and/or stored separately from article of clothing 100.

In some embodiments, article of clothing 100 includes an optional control circuit 130 (such as a processor) that coordinates functions of article of clothing 100, such as conveying or providing: the activation command, the deactivation command, the activation signal, the deactivation command, the feedback, the encouragement, and/or communication via interface circuit 128 (such as measurements of the milk flow rate and/or the volume of collected milk).

Figure 3:
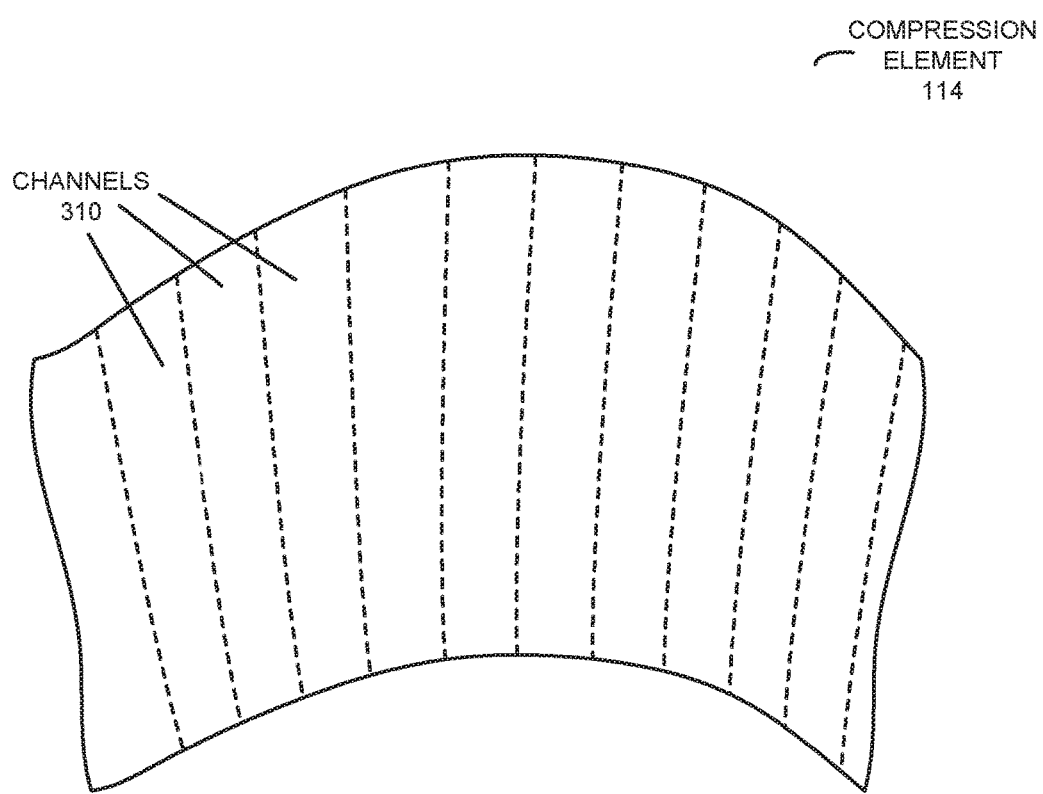
FIG. 3 is a block diagram illustrating a compression element for use in the article of clothing of FIG. 1 in accordance with an embodiment of the present disclosure.

FIG. 3 presents a block diagram illustrating a compression element 114. This compression element may include channels 310 that, during operation, are used to generate the type of compression pattern. For example, compression element 114 may generate the type of compression pattern by selectively filling or emptying one or more of channels 310 using a gas and/or a liquid. Note that while radial channels 310 are shown in FIG. 3, in other embodiments different channel shapes and/or configurations are used. Moreover, note that compression element 114 may include a sleeve that can be wrapped around breast 200 (FIG. 2) to encompass a portion of breast 200 (FIG. 2), such as around a circumference of a portion of breast 200 (FIG. 2). Alternatively or additionally, compression element 114 may include bearings (such as ball bearings), and during operation compression element 114 may generate the type of compression pattern using the bearings.

Figure 4:
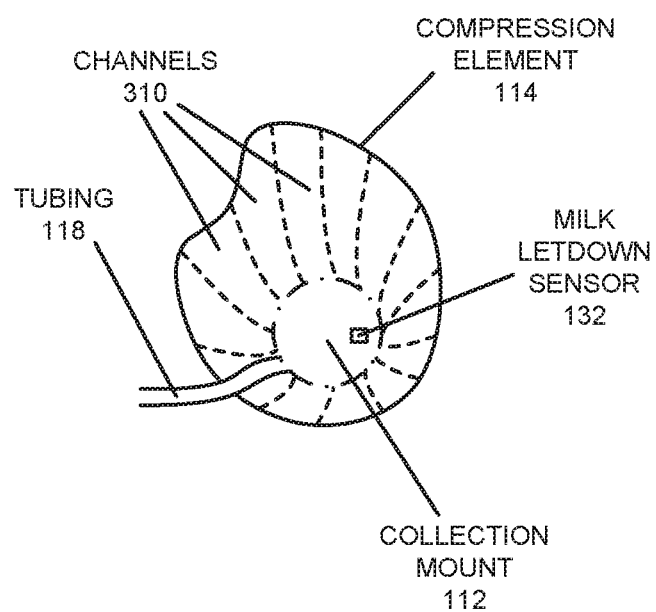
FIG. 4 is a drawing illustrating a front view of a breast and the compression element of FIG. 3 in accordance with an embodiment of the present disclosure.

FIG. 4 presents a drawing illustrating a front view of breast 200 and compression element 114. By varying the compression at one or more locations on breast 200 as a function of time, compression element 114 may generate the type of compression pattern. Note that the type of compression pattern may include: a circular pattern around a circumference of breast 200, a spiral pattern around a circumference of breast 200 that moves from proximal to distal towards the areola, a rhythmic pattern (such as one that includes one or more fundamental frequencies), a random pattern (in terms of locations on breast 200, amplitude and/or frequencies), a massage pattern, a programmable pattern (which may be provided remotely via interface circuit 128 in FIG. 1 and/or which may be selected by the individual), and/or a localized pattern (such as a particular location on breast 200, such as proximate to the areola). Moreover, as noted previously, the type of compression pattern, an amplitude of the compression pattern and/or the location may be selectable by the individual.

In an exemplary embodiment, reservoir 120 (FIG. 1) includes a disposable fabric reservoir or bag. Alternatively, another type of storage unit may be used, such as a bottle. Therefore, the reservoir may be used to deliver milk to a baby or an infant, thereby eliminating the need to transfer milk between a pumping container to a bottle or another delivery container. In some embodiments, a nipple and/or a lid is included or attached to the reservoir. The nipple and/or lid may be changed, thereby allowing the size to be changed and/or to adapt to the needs of the baby or the infant, such as if the baby is in the hospital.

However, in other embodiments, the reservoir is fixed in the article of clothing. Moreover, the reservoir may include compartments, which may allow lids, nipples, cleaning tools, repair tools, paper towels, and other items to be safely housed together with the reservoir. Therefore, instead of one reservoir, there may be multiple reservoirs. For example, a 'popsicle holder' type of storage may be provided in which the milk is put into multiple reservoirs or containers. This approach may allow the milk to be given in smaller quantities, thereby preserving the remaining milk for a later time. In addition, multiple reservoirs may facilitate storage because it allows more flexibility in the amount of milk that remains with the individual and the quantity (and thus weight) of milk that gets stored subsequent use. In some embodiments, the reservoir includes channels in the article of clothing. These channels may have different colors or labels that indicate a time when the milk was collected in a given channel and/or a temperature of the milk.

Furthermore, the reservoir may have a wide variety of shapes, thereby allowing it to provide both function and fashion. For example, the reservoir may take on the form of a camelback vest that includes one or more small channels of a coolant interwoven with one or more channels of breast milk. In this way, the breast milk may be maintained at a relatively cool or constant temperature that is desired. Alternatively or additionally, a heat source may be used to achieve the desired temperature. Note that the channels may have a variety of shapes, such as oblong forms, cylinders or other forms. The channels may be removable, so that they can be cleaned and/or stored. This may also allow the article of clothing to be used for other purposes, such as hiking. Note that the coolant may include a liquid (such as water, oil or another liquid) and/or a gas with suitable thermodynamic properties. The pump element that is coupled to the reservoir may also provide a mechanism for 'self-cleaning' of the reservoir (such as a purge or steam-clean) to obviate the need for separate cleaning of the reservoir.

While the preceding embodiments illustrated the article of clothing including the reservoir, in some embodiments off-body storage is used, such as: in a purse, a backpack, a fanny pack, high tops, thigh bag, an arm band, and/or a hat.

In addition to detecting milk letdown, or measuring the milk flow rate or the volume of milk collected, the article of clothing may include a sensor that measures (or may receive information that specifies): the time elapsed since milk was last collected, breast temperature, another parameter related to the breast, etc. Note that the sensors in the article of clothing may be at one or more locations, i.e., the sensors may be localized or distributed, within the article of clothing (such as on its associated components) and/or on the individual's body (on the breast or another area, such as the stomach, neck, arms, back, flank, etc.).

Optional feedback device 134 (FIG. 1) may allow automated reminders to be provided to the individual, such as a reminder after a time interval since a last breast-pumping session has occurred. Reminders may be provided in a variety of forms, such as a physiological signal (such as a noise, a vibration, an audible message, etc.), and/or a message communicated to the electronic device (such as an email, a text, a phone alert, etc.).

In some embodiments, the article of clothing includes passive and/or active components that reduce or mask the sound associated with operation of the article of clothing. For example, the article of clothing may include acoustic insulation (such as sound-proof foam) and/or muffler. However, in other embodiments these components are external to the article of clothing. Moreover, active sound cancellation or sound masking may be used, such as a white-noise generator and a speaker.

In order to encourage milk production and milk letdown, in some embodiments the article of clothing mechanically (such as by massaging or providing pressure to the nipple or a pressure point e.g., GB21, or providing a small amount of fluid to the nipple), electrically and/or chemically stimulates a portion of the breast (such as the nipple). For example, a hormone or another stimulant may be provided that encourages milk letdown.

Although article of clothing 100 in FIG. 1 is shown as including pump 116, in other embodiments pump 116 is separate from article of clothing 100. For example, pump 116 is remotely located, such as in a separate room. A pump case may be personalized to make it unique to the individual. For example, the pump case may include an electronic image or a photograph of a baby or an infant. This may provide a visual stimulus that helps promote breast-milk production. Furthermore, instead of using one pump, in alternating fashion, between breasts, there may two pumps (one for each breast). However, in some embodiments, a single pump may be used, and the breasts may be pumped sequentially. This configuration may provide a smaller form factor with reduced power consumption and noise.

In some embodiments, a cleaning tool is provided with pump 116 (FIG. 1). For example, the cleaning tool may include a cleaning element attached to a heating device that steam cleans the pump and the associated tubing. Moreover, pump 116 may be plugged into the cleaning tool in order to be cleaned and sterilized. This approach may eliminate the need for a user (such as the individual) to remove and reassemble components, or to scrub and dry the components. However, in some embodiments components in the article of clothing reduce or eliminate the need for cleaning. For example, a hard plastic (such as a thermoset plastic) and/or silver-coated materials may be used.

Figure 5:
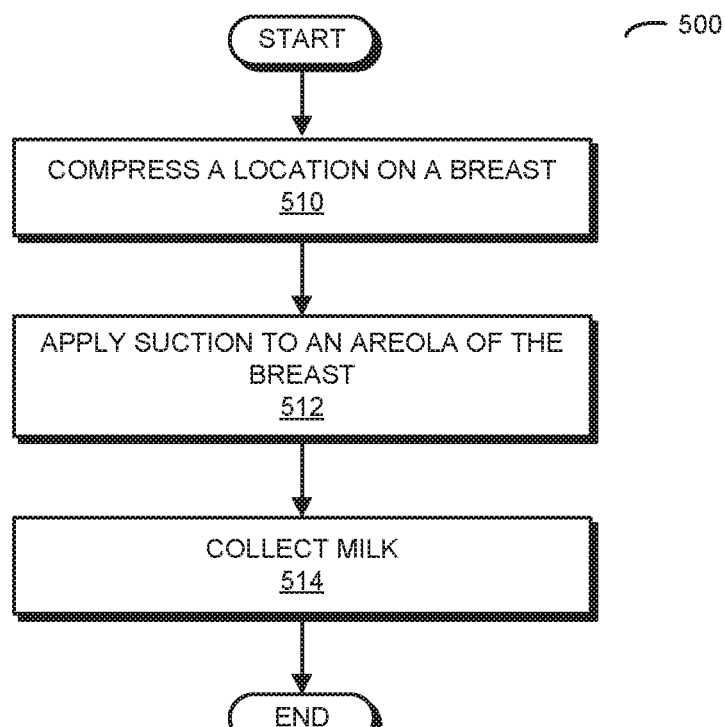
FIG. 5 is a flow diagram illustrating a method for collecting milk from a breast using an article of clothing in accordance with an embodiment of the present disclosure.

We now describe a method for using the article of clothing. FIG. 5 presents a flow diagram illustrating a method 500 for collecting milk from a breast using an article of clothing, such as article of clothing 100 (FIG. 1). During operation of the article of clothing, a compression element may compress a location on the breast (operation 510) to facilitate lactation using a type of compression pattern. Moreover, a pump mechanically coupled by tubing to a collection mount in the article of clothing may apply suction to an areola of the breast (operation 512). Next, a reservoir in the article of clothing collects the milk (operation 514) based on the compression and the suction.

In these ways, the article of clothing and the breast-pumping technique may allow a woman to breast pump when she wants to (such as at a time and place that is convenient, including while she is at work), and in an efficient and a discrete manner. Moreover, the article of clothing may reduce the woman's frustration and may improve her overall user experience while breast pumping. Consequently, the article of clothing may encourage breast pumping, with the commensurate health benefits for babies and infants.

Figure 6:
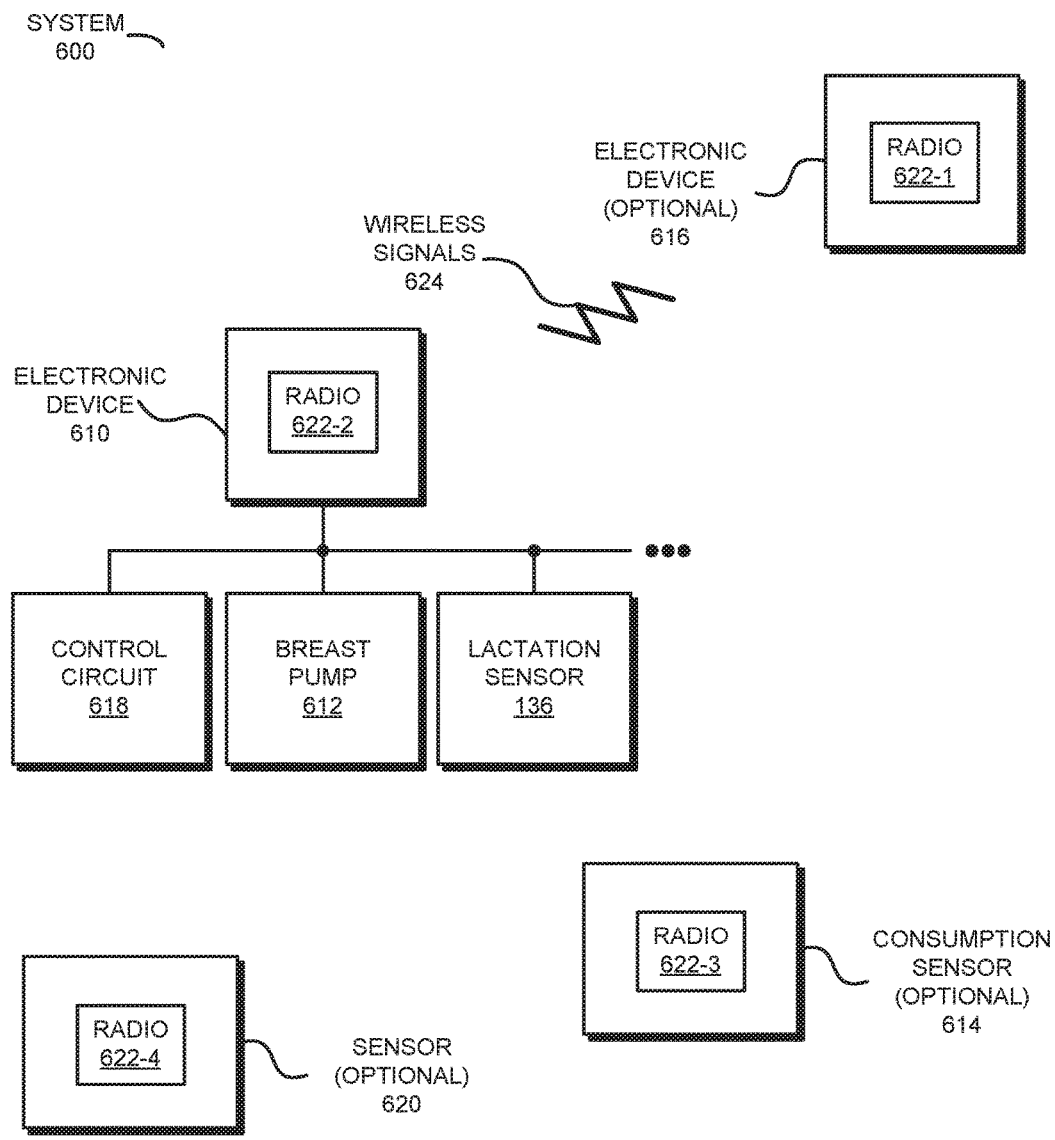
FIG. 6 is a block diagram illustrating a system in accordance with an embodiment of the present disclosure.

We now describe embodiments of the system, which may be used in conjunction with or separately from the article of clothing. FIG. 6 presents a block diagram illustrating a system 600. This system includes: a breast pump 612, lactation sensor 136, electronic device 610 that communicates with one or more electronic devices (such as optional consumption sensor 614 associated with optional bottle 700 in FIG. 7 and/or optional electronic device 616), and a control circuit 618. During operation, breast pump 612 collects milk from an individual during one or more breast-pumping sessions. Moreover, lactation sensor 136 measures a volume of the collected milk as a function of time. Furthermore, electronic device 610 receives information (e.g., from optional consumption sensor 614 and/or optional electronic device 616) specifying milk consumption by a second individual (such as a baby or an infant) as a function of time. Additionally, control circuit 618 determines a need for milk based on a temporal pattern of the volume of the collected milk and a temporal pattern of the milk consumption, and provides feedback based on the determined need for milk that synchronizes the one or more breast-pumping sessions and the milk consumption.

For example, the feedback may be provided using optional feedback device 134. Alternatively or additionally, as described further below with reference to FIGS. 8 and 9, the feedback may be provided to optional electronic device 616 (e.g., for display on a user interface). Note that the feedback may alert the individual to initiate a breast-pumping session. (In addition, as noted previously, the feedback may provide encouragement to the individual while breast pumping, such as a summary of the amount of milk collected.) Alternatively or additionally, the feedback may include a signal to breast pump 612 that initiates a breast-pumping session without action by the individual (e.g., automatically). In some embodiments, the individual can manually override a determination by control circuit 618 to initiate a breast-pumping session (e.g., the individual may stop a breast-pumping session that occurs at an inopportune time, may reinitiate a previously stopped breast-pumping session, or may specify a predefined delay until starting a breast-pumping session).

In some embodiments, control circuit 618 determines the need for milk based on one or more additional inputs. For example, system 600 may include an optional sensor 620. During operation, optional sensor 620 may measure: a vital sign of the individual as a function of time, a biomarker of the individual as a function of time, and/or an activity pattern of the individual as a function of time (such as a sleep pattern, an eating or dietary pattern, an exercise pattern, a sedentary pattern, etc.). For example, optional sensor 620 may measure: a pulse rate, a respiration rate, blood pressure, skin temperature, skin electrical conductivity, chemical analysis of a biological sample (such as sweat, saliva or blood), gene-expression analysis of a biological sample, ribonucleic-acid analysis of a biological sample and/or deoxyribonucleic-acid of a biological sample. The optional sensor may measure a wide variety of biomarkers, such as: an electroencephalogram signal, an electromyography signal, one or more electrolytes (e.g., sodium, chloride, potassium, and/or calcium), one or more metabolites (e.g., lactate, creatinine, glucose, and/or uric acid), and/or one or more small molecules (e.g., an amino acid, a steroid or a hormone, cortisol, a protein, an interleukin, and/or a neuropeptides). Alternatively or additionally, the vital-sign measurements, the biomarker and/or the activity pattern may be received by electronic device 610. Similarly, electronic device 610 may receive additional information specifying: a vital sign of the second individual as a function of time, a biomarker of the second individual as a function of time, and/or an activity pattern of the second individual as a function of time. Then, control circuit 618 may determine the need for milk based on: a temporal pattern of the vital sign of the individual, a temporal pattern of the biomarker of the individual, a temporal pattern of the activity pattern of the individual, a temporal pattern of the vital sign of the second individual, a temporal pattern of the biomarker of the second individual, and/or a temporal pattern of the activity pattern of the second individual.

Moreover, control circuit 618 may determine the need for milk based on a day of the week (and, more generally, a timestamp). For example, a woman's lactation may be different on the weekend than during the workweek. Furthermore, the information received by electronic device 610 may specify: a temperature of milk in optional bottle 700 (FIG. 7), and/or a time duration since the milk in optional bottle 700 (FIG. 7) was collected (which may indicate whether the milk is still usable). Control circuit 618 may, therefore, determine the need for milk based on: the temperature of the milk in optional bottle 700 (FIG. 7), and/or the time duration.

Note that control circuit 618 may determine the need for milk using a supervised-learning model that relates the need for milk with one or more of the preceding inputs. For example, the supervised-learning model, which may be developed using a wide variety of supervised-learning techniques, may include: a neural network, LASSO (a regularized linear regression technique like ridge regression, but with $L_1$-norm regularization of the coefficients), a decision tree (such as classification and regression trees, with or without gradient boosting), a support vector machine, a model developed using Bayesian statistical analysis, least-squares regression, logistic regression, a non-parametric multivariate analysis technique, etc. Moreover, the supervised-learning technique may include a linear or a non-linear kernel. In some embodiments, the supervised-learning model is determined using data from one or more other individuals, such as by using collaborative filtering.

In addition to initiating a breast-feeding session when a need for milk is determined, control circuit 188 may initiate a breast-pumping session: after a predefined time interval since a previous breast-feeding session (such as one hour, two hours, three hours, etc.), according to a predefined schedule, according to user preferences (such as different time intervals during the day or at night, or for different days of the week) and/or randomly after a minimum time interval (such as one hour) since a previous breast-feeding session. For example, the predefined schedule may systematically increase the time interval between breast-pumping sessions, such as when an infant is being weaned off of breast milk.

While preceding embodiments illustrated automated collection of data using sensors or receiving information from one or more electronic devices, in other embodiments at least some of the data used by control circuit 618 is entered manually using a user interface (such as a keyboard, a user-interface device, a user interface displayed on a touch-sensitive display, voice recognition, etc.). In some embodiments, at least some of the data used by control circuit 618 is automatically generated based on a time of a most-recent feeding and a predefined feeding schedule and/or predefined user feeding preferences (such as one or more time intervals between feedings).

As noted previously, electronic device 610 and optional electronic device 616 may include radios that communicate packets or frames in accordance with one or more communication protocols, such as: an Institute of Electrical and Electronics Engineers (IEEE) 802.11 standard (which is sometimes referred to as 'Wi-Fi®,' from the Wi-Fi® Alliance of Austin, Tex.), Bluetooth® (from the Bluetooth Special Interest Group of Kirkland, Wash.), a cellular-telephone communication protocol, a near-field-communication standard or specification (from the NFC Forum of Wakefield, Mass.), and/or another type of wireless interface.

For example, the cellular-telephone communication protocol may include or may be compatible with: a $2^{nd}$ generation or mobile telecommunication technology, a $4^{rd}$ generation of mobile telecommunications technology (such as a communication protocol that complies with the International Mobile Telecommunications-2000 specifications by the International Telecommunication Union of Geneva, Switzerland), a $4^{th}$ generation of mobile telecommunications technology (such as a communication protocol that complies with the International Mobile Telecommunications Advanced specification by the International Telecommunication Union of Geneva, Switzerland), and/or another cellular-telephone communication technique. In some embodiments, the communication protocol includes Long Term Evolution or LTE. However, a wide variety of communication protocols may be used. In addition, the communication may occur via a wide variety of frequency bands.

As shown in FIG. 6, during operation electronic device 610 and optional electronic device 616 may wirelessly communicate while: transmitting advertising frames on wireless channels, detecting one another by scanning wireless channels, establishing connections (for example, by transmitting association requests), and/or transmitting and receiving packets or frames (which may include the association requests and/or additional information as payloads, such as commands, measurements, feedback, etc.).

Figure 11:
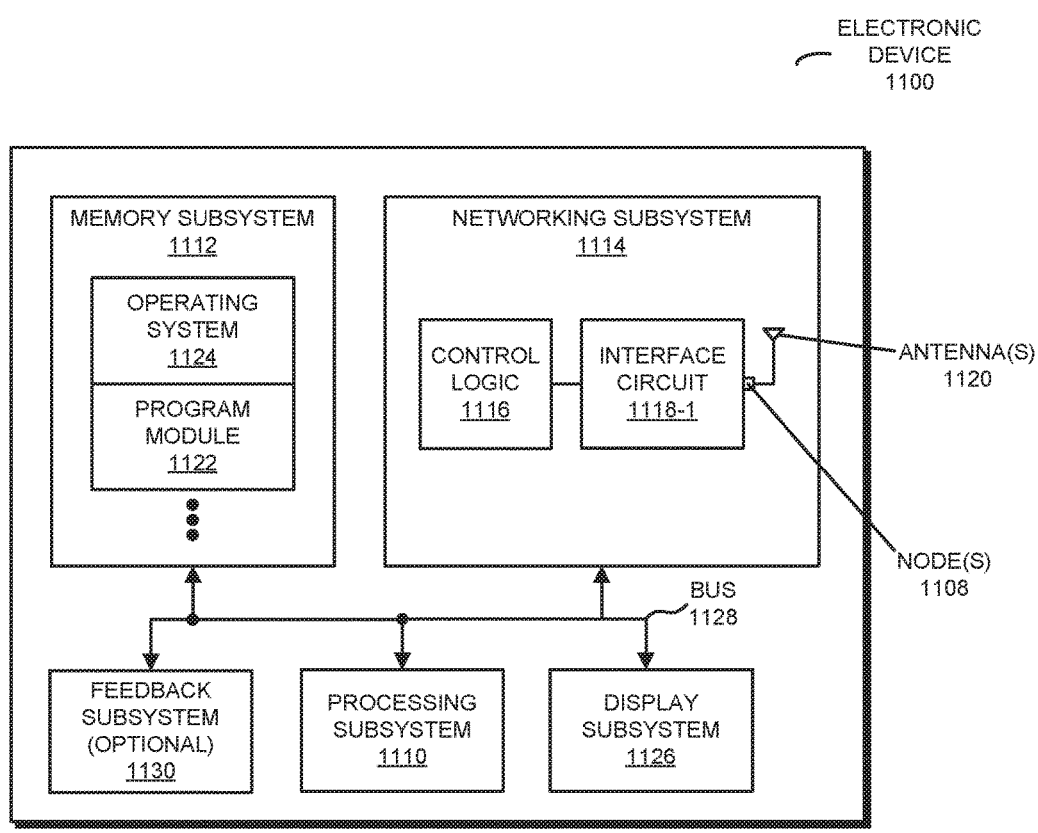
FIG. 11 is a block diagram illustrating an electronic device in accordance with an embodiment of the present disclosure.

Moreover, as described further below with reference to FIG. 11, electronic device 610 and optional electronic device 616 may include subsystems, such as: a networking subsystem, a memory subsystem and a processor subsystem. In addition, electronic device 610 and optional electronic device 616 may include radios 622 in the networking subsystems (such as interface circuit 128 in FIG. 1). (Note that radios 622 may be instances of the same radio or may be different from each other.) More generally, electronic device 610 and optional electronic device 616 can include (or can be included within) any electronic devices with the networking subsystems that enable electronic device 610 and optional electronic device 616 to wirelessly communicate with each other. This wireless communication can comprise transmitting advertisements on wireless channels to enable electronic devices to make initial contact or detect each other, followed by exchanging subsequent data/management frames (such as association requests and responses) to establish a connection, configure security options (e.g., Internet Protocol Security), transmit and receive packets or frames via the connection, etc.

As can be seen in FIG. 1, wireless signals 624 (represented by a jagged line) are transmitted from radio 622-1 in optional electronic device 616. These wireless signals are received by electronic device 610. In particular, optional electronic device 616 may transmit packets. In turn, these packets may be received by a radio 622-2 in electronic device 610. This may allow optional electronic device 616 to communicate information to electronic device 610. While FIG. 1 illustrates optional electronic device 616 transmitting packets, note that optional electronic device 616 may also receive packets from electronic device 610.

In the described embodiments, processing of a packet or frame in electronic device 610 includes: receiving wireless signals 624 with the packet or frame; decoding/extracting the packet or frame from received wireless signals 624 to acquire the packet or frame; and processing the packet or frame to determine information contained in the packet or frame (such as the information or the additional information).

Although we describe the network environment shown in FIG. 1 as an example, in alternative embodiments, different numbers or types of electronic devices may be present. For example, some embodiments comprise more or fewer electronic devices. As another example, in another embodiment, different electronic devices are transmitting and/or receiving packets or frames. While electronic device 610 and optional electronic device 616 are illustrated with a single instance of radios 622, in other embodiments electronic device 610 and optional electronic device 616 may include multiple radios.

Figure 7:
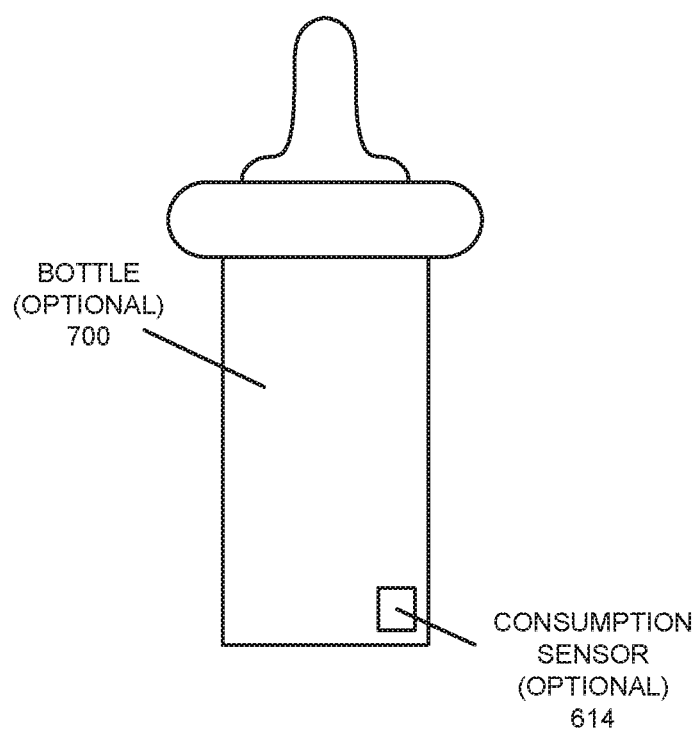
FIG. 7 is a block diagram illustrating a bottle with a consumption sensor in accordance with an embodiment of the present disclosure.

FIG. 7 presents a block diagram illustrating a bottle 700 with an optional consumption sensor 614. As noted previously, optional consumption sensor 614 may measure or determine absolute or relative milk consumption by the second individual, and may communicate this information to electronic device 610 (FIG. 6). For example, optional consumption sensor 614 may include: an accelerometer, a velocity sensor, a position sensor, an orientation sensor (such as a gyroscope), an optical sensor, a flow sensor, a level sensor, and/or a resistance sensor. In an exemplary embodiment, when bottle 700 is tipped back by at least 45°, optional consumption sensor 614 may indicate that the baby or infant is feeding, as well as a timestamp when the feeding started (and/or ended). Alternatively or additionally, removing bottle 700 from a refrigerator and/or heating bottle 700 may cause optional consumption sensor 614 to communicate that feeding is about to start.

Figure 8:
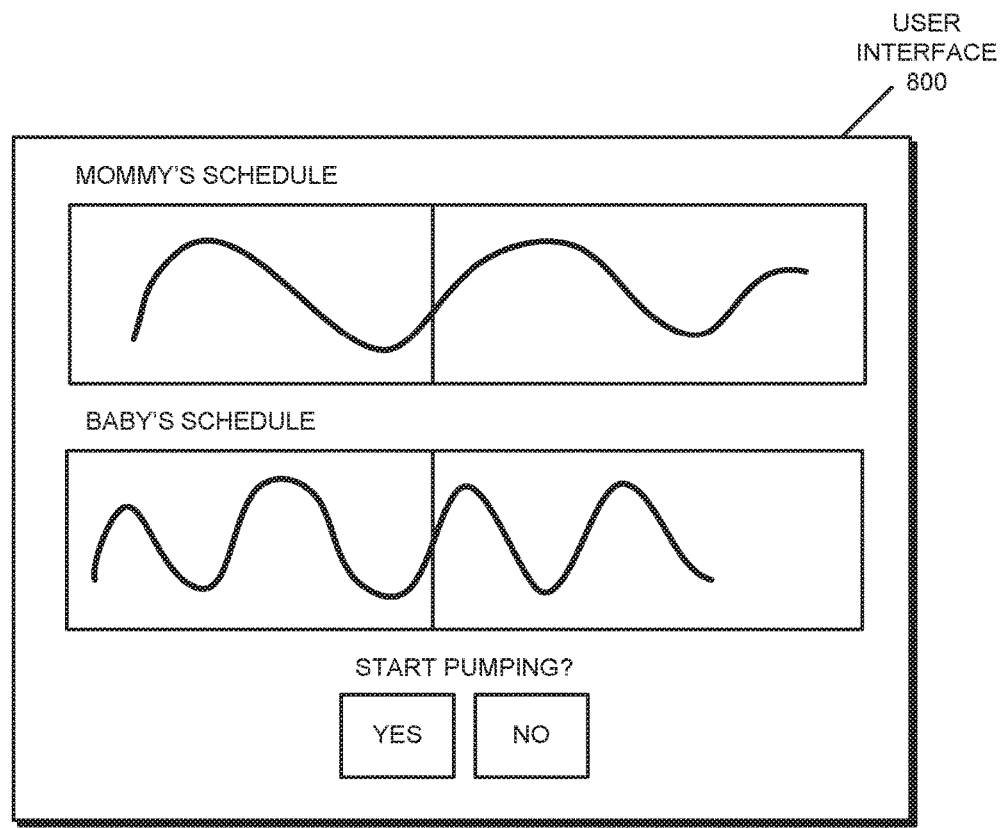
FIG. 8 is a block diagram illustrating a user interface in an electronic device in the system of FIG. 6 in accordance with an embodiment of the present disclosure.

In some embodiments, the feedback is communicated to optional electronic device 616, and is then displayed on a user interface. This is shown in FIG. 8, which presents a block diagram illustrating a user interface 800 in optional electronic device 616 (FIG. 6). In particular, user interface 800 may include a woman's time-varying lactation cycle or pattern and a baby or infant's time-varying consumption cycle or pattern, along with an option to initiate a breast-pumping session by activating a virtual icon (e.g., by touching a display screen within a strike area associated with the virtual icon). Alternatively or additionally, electronic device 616 (FIG. 6) may include a button or a knob that can be used to initiate a breast-pumping session. In general, information about the woman's lactation cycle and the baby or infant's consumption cycle may include: a graph, a table, a chart, summary statistics, etc.

Figure 9:
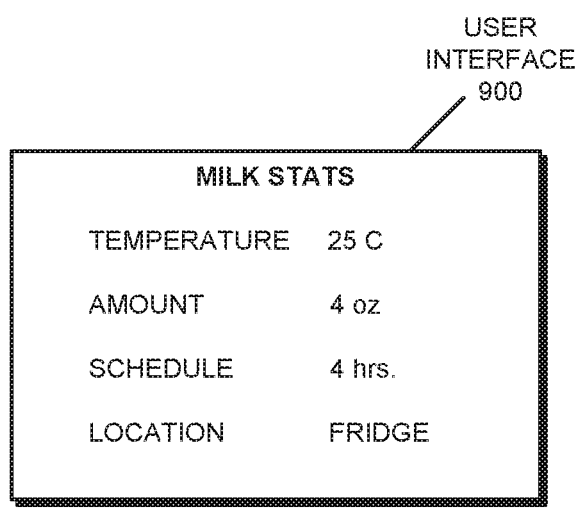
FIG. 9 is a block diagram illustrating a user interface in an electronic device in the system of FIG. 6 in accordance with an embodiment of the present disclosure.

FIG. 9 presents a block diagram illustrating a user interface 900 in optional electronic device 616 (FIG. 6) that displays statistical information about collected milk, such as: temperature, amount or volume of milk (such as milk consumed, milk remaining, etc.), how long the milk can be used for (or is expected to last) and a location where the milk is currently stored.

Note that other information may be display to assist the individual. For example, the other information may include information about: a lactation consultant, a childcare provider, freezing suggestions, breast-pumping or breast-feeding education and/or a portal or link to a user community, a chat room or a social network. Furthermore, system 600 (FIG. 6) may use optional electronic device 616 (FIG. 6) to present advice to the individual based on what works best for them or other women, such as: positions, types of compression patterns, a likely or probable breast-pumping schedule (so the individual can plan their day), an estimate of the cost savings obtained by breast pumping (as opposed to buying an equivalent volume of formula), etc. Collectively, this information may provide encouragement and support to the individual.

In an exemplary embodiment, the system includes sensors or uses sensor data that is received from other electronic devices for parameters such as: breast skin temperature, ambient temperature, pressure, humidity, position, etc. These measurements may be used in supervised or machine learning of the pumping technique. The system may learn and remember lessons from prior breast-pumping session and may cumulatively apply them to future sessions, so that the learning is 'across' and 'between' sessions, not just 'within' a session.

The sensor data may include flow and/or volume sensing of expressed milk that occurs 'in-line' or 'at the level of the stream' as opposed to 'on-bottle.' This may allow the collected milk to be monitored even when the milk is collected in a non-rigid container as envisioned with a wearable device.

In some embodiments, the reservoir is adaptable or a one-size fits all reservoir that can be used with any pump size. The reservoir may be wearable beyond pumping times, and may refrigerate milk while keeping the skin warm.

The system may allow pumping automation to synchronization with the baby's feed times/durations (including knowing when the baby is feeding at a remote location) and is able to alert the mother (at a minimum) to pump or actually initiate pumping in synchronization with the baby's feedings. Thus, there may be one or more sensors on the baby or baby's bottle to synchronize with the pump via a network.

Sound insulation or sound cancellation may be used with the breast pump so that it is less noisy.

As noted previously, machine learning may be used with the sensor data, including determining what you want to sense, calculate, learn, and 'do' with the learning. This may achieve faster let-down by monitoring a mother's breast (at pump) conditions (such as heat, humidity, temp, etc.) and also on her body (such as stress levels via wearables measuring heart rate, perspiration, activity, etc.) and/or provide stimulation (such as even music, messages, pictures via cellphone) to improve her mental state. In addition, the system may sense the response to off-the-shelf stimulation to determine what rate, rhythm, and intensity of suction intensifies let down and under what conditions.

The system may incorporate breast massage with the wearable device and/or with machine learning. For example, the machine learning may determine the best massage pattern to optimize let down and shorten pump duration while increasing the milk extracted. Alternatively or additionally, pressure points, heat and/or vibration may be used to stimulate the breast.

Figure 10:
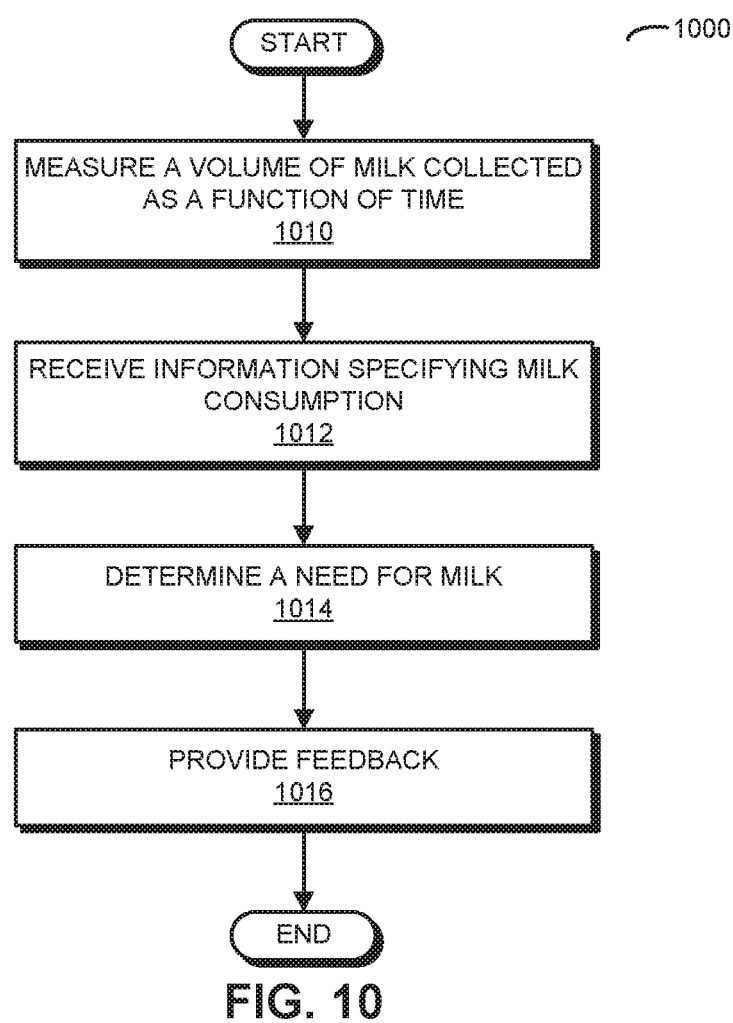
FIG. 10 is a flow diagram illustrating a method for synchronizing one or more breast-pumping sessions of an individual and milk consumption by a second individual in accordance with an embodiment of the present disclosure.

We now describe another method. FIG. 10 presents a flow diagram illustrating a method 1000 for synchronizing one or more breast-pumping sessions of an individual and milk consumption by a second individual, which may be performed using one or more electronic devices in a system, such as electronic device 610 in system 600 (FIG. 6). During operation, the system measures, using a lactation sensor, a volume of milk collected as a function of time (operation 1010) using a breast pump, where the breast pump collects the milk from the individual during the one or more breast-pumping sessions. For example, the measurements may be at discrete times or they may be performed continuously. Then, the system receives, from a consumption sensor associated with a bottle, information specifying the milk consumption as a function of time (operation 1012). Similarly, the milk consumption may be specified at discrete times or continuously. Moreover, the system determines a need for milk (operation 1014) based on a temporal pattern of the volume of the collected milk and a temporal pattern of the milk consumption. Next, the system provides feedback (operation 1016) based on the determined need for milk that synchronizes the one or more breast-pumping sessions and the milk consumption.

In these ways, the system and the breast-pumping technique may allow women to breast pump in an efficient and effective manner. For example, by synchronizing supply and demand, and by taking into account temporal variations in a woman's milk production, the system may increase a mother's milk production. In particular, the system (such as the feedback provided during breast pumping) may maximize an average volume of the milk collected during a given breast-pumping session. Moreover, the system may reduce the woman's frustration and may improve her overall user experience while breast pumping. Consequently, the system may encourage breast pumping, with the commensurate health benefits for babies and infants.

In some embodiments of methods 500 (FIG. 5) and/or 1000, there may be additional or fewer operations. Moreover, the order of the operations may be changed, and/or two or more operations may be combined into a single operation.

We now describe embodiments of an electronic device. FIG. 11 presents a block diagram illustrating an electronic device 1100, such as one or more components in article of clothing 100 (FIG. 1), electronic device 610 and/or optional electronic device 616. This electronic device includes processing subsystem 1110, memory subsystem 1112, and networking subsystem 1114. Processing subsystem 1110 includes one or more devices configured to perform computational operations. For example, processing subsystem 1110 can include one or more microprocessors, application-specific integrated circuits (ASICs), microcontrollers, programmable-logic devices, and/or one or more digital signal processors (DSPs). One or more of these components in processing subsystem are sometimes referred to as a 'control mechanism' or a 'control circuit' (such as control circuit 618 in FIG. 6).

Memory subsystem 1112 includes one or more devices for storing data and/or instructions for processing subsystem 1110 and networking subsystem 1114. For example, memory subsystem 1112 can include dynamic random access memory (DRAM), static random access memory (SRAM), and/or other types of memory. In some embodiments, instructions for processing subsystem 1110 in memory subsystem 1112 include: one or more program modules or sets of instructions (such as program module 1122 or operating system 1124), which may be executed by processing subsystem 1110. Note that the one or more computer programs may constitute a computer-program mechanism. Moreover, instructions in the various modules in memory subsystem 1112 may be implemented in: a high-level procedural language, an object-oriented programming language, and/or in an assembly or machine language. Furthermore, the programming language may be compiled or interpreted, e.g., configurable or configured (which may be used interchangeably in this discussion), to be executed by processing subsystem 1110.

In addition, memory subsystem 1112 can include mechanisms for controlling access to the memory. In some embodiments, memory subsystem 1112 includes a memory hierarchy that comprises one or more caches coupled to a memory in electronic device 1100. In some of these embodiments, one or more of the caches is located in processing subsystem 1110.

In some embodiments, memory subsystem 1112 is coupled to one or more high-capacity mass-storage devices (not shown). For example, memory subsystem 1112 can be coupled to a magnetic or optical drive, a solid-state drive, or another type of mass-storage device. In these embodiments, memory subsystem 1112 can be used by electronic device 1100 as fast-access storage for often-used data, while the mass-storage device is used to store less frequently used data.

Networking subsystem 1114 includes one or more devices configured to couple to and communicate on a wired and/or wireless network (i.e., to perform network operations), including: control logic 1116, interface circuit 1118 and associated antenna(s) 1120. (While FIG. 11 includes antenna(s) 1120, in some embodiments electronic device 1100 includes one or more nodes, such as node(s) 1108, e.g., pads, which can be coupled to antenna(s) 1120. Thus, electronic device 1100 may or may not include antenna(s) 1120.) For example, networking subsystem 1114 can include a Bluetooth networking system, a cellular networking system (e.g., a 3G/4G network such as UMTS, LTE, etc.), a universal serial bus (USB) networking system, an Institute of Electrical and Electronics Engineers (IEEE) 802.15 standard (such as ZigBee® from the ZigBee® Alliance of San Ramon, Calif.), a networking system based on the standards described in IEEE 802.11 (e.g., a Wi-Fi networking system), an Ethernet networking system, and/or another networking system. Note that the combination of interface circuit 1118 and at least one of antenna(s) 1120 may constitute a radio. In some embodiments, networking subsystem 1114 communicates with one or more electronic devices via a wired interface.

Networking subsystem 1114 includes processors, controllers, radios/antennas, sockets/plugs, and/or other devices used for coupling to, communicating on, and handling data and events for each supported networking system. Note that mechanisms used for coupling to, communicating on, and handling data and events on the network for each network system are sometimes collectively referred to as a 'network interface' for the network system. Moreover, in some embodiments a 'network' between the electronic devices does not yet exist. Therefore, electronic device 1100 may use the mechanisms in networking subsystem 1114 for performing simple wireless communication between the electronic devices, e.g., transmitting advertising or beacon frames and/or scanning for advertising frames transmitted by other electronic devices as described previously.

Within electronic device 1100, processing subsystem 1110, memory subsystem 1112, and networking subsystem 1114 are coupled together using bus 1128. Bus 1128 may include an electrical, optical, and/or electro-optical connection that the subsystems can use to communicate commands and data among one another. Although only one bus 1128 is shown for clarity, different embodiments can include a different number or configuration of electrical, optical, and/ or electro-optical connections among the subsystems.

In some embodiments, electronic device 1100 includes a display subsystem 1126 for displaying information on a display (such as the communication warning message), which may include a display driver, an I/O controller and the display, such as a liquid-crystal display, a multi-touch touchscreen (which is sometimes referred to as a touch-sensitive display), etc.

Electronic device 1100 can be (or can be included in) any electronic device with at least one network interface. For example, electronic device 1100 can be (or can be included in): a desktop computer, a laptop computer, a subnotebook/ netbook, a tablet computer, a smartphone, a cellular telephone, a smartwatch, a portable computing device, and/or another electronic device.

Although specific components are used to describe electronic device 1100, in alternative embodiments, different components and/or subsystems may be present in electronic device 1100. For example, electronic device 1100 may include one or more additional processing subsystems, memory subsystems, networking subsystems, display subsystems, one or more I/O interfaces and/or optional feedback subsystem 1130. Moreover, one or more of the subsystems may not be present in electronic device 1100. Furthermore, in some embodiments, electronic device 1100 may include one or more additional subsystems that are not shown in FIG. 11 (such as a power subsystem with a non-rechargeable or a rechargeable power source). Also, although separate subsystems are shown in FIG. 11, in some embodiments, some or all of a given subsystem or component can be integrated into one or more of the other subsystems or component(s) in electronic device 1100. For example, in some embodiments program module 1122 is included in operating system 1124. More generally, two or more components may be combined into a single component or a single electronic device.

Moreover, the circuits and components in electronic device 1100 may be implemented using any combination of analog and/or digital circuitry, including: bipolar, PMOS and/or NMOS gates or transistors. Furthermore, signals in these embodiments may include digital signals that have approximately discrete values and/or analog signals that have continuous values. Additionally, components and circuits may be single-ended or differential, and power supplies may be unipolar or bipolar.

An integrated circuit may implement some or all of the functionality of networking subsystem 1114, such as one or more radios. Moreover, the integrated circuit may include hardware and/or software mechanisms that are used for transmitting wireless signals from electronic device 1100 and receiving signals at electronic device 1100 from other electronic devices. Aside from the mechanisms herein described, radios are generally known in the art and hence are not described in detail. In general, networking subsystem 1114 and/or the integrated circuit can include any number of radios.

In some embodiments, networking subsystem 1114 and/or the integrated circuit include a configuration mechanism (such as one or more hardware and/or software mechanisms) that configures the radios to transmit and/or receive on a given channel (e.g., a given carrier frequency). For example, in some embodiments, the configuration mechanism can be used to switch the radio from monitoring and/or transmitting on a given channel to monitoring and/or transmitting on a different channel. (Note that 'monitoring' as used herein comprises receiving signals from other electronic devices and possibly performing one or more processing operations on the received signals, e.g., determining if the received signal comprises an advertising frame, etc.)

The described embodiments may be used in a variety of network interfaces. Furthermore, while some of the operations in the preceding embodiments were implemented in hardware or software, in general the operations in the preceding embodiments can be implemented in a wide variety of configurations and architectures. Therefore, some or all of the operations in the preceding embodiments may be performed in hardware, in software or both. For example, at least some of the operations in the breast-pumping technique may be implemented using program module 1122, operating system 1124 (such as drivers for interface circuit 1118) and/or in firmware in interface circuit 1118. Alternatively or additionally, at least some of the operations in the breast-pumping technique may be implemented in a physical layer, such as hardware in interface circuit 1118.

In the preceding description, we refer to 'some embodiments.' Note that 'some embodiments' describes a subset of all of the possible embodiments, but does not always specify the same subset of embodiments.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. A computer-program product for use in conjunction with an electronic device, the computer-program product comprising a non-transitory computer-readable storage medium and a computer-program mechanism embedded therein to synchronize one or more breast-pumping sessions of an individual and milk consumption by a second individual, the computer-program mechanism including:
   instructions for measuring, using a lactation sensor, a volume of milk collected as a function of time using a breast pump, wherein the breast pump collects the milk from the individual during the one or more breast-pumping sessions;
   instructions for receiving, from a consumption sensor associated with a bottle, information specifying the milk consumption as a function of time;
   instructions for determining a need for milk based on a temporal pattern of the volume of the collected milk and a temporal pattern of the milk consumption; and
   instructions for providing feedback based on the determined need for milk that synchronizes the one or more breast-pumping sessions and the milk consumption.

2. The computer-program product of claim 1, wherein the feedback alerts the individual to initiate a breast-pumping session.

3. The computer-program product of claim 1, wherein the feedback includes a signal to the breast pump that initiates a breast-pumping session.

4. The computer-program product of claim 1, wherein the computer-program mechanism comprises instructions for measuring, using a sensor, one of: a vital sign of the individual as a function of time, a biomarker of the individual as a function of time, and an activity pattern of the individual as a function of time; and
   wherein determining the need for milk is based on one of: a temporal pattern of the vital sign, a temporal pattern of the biomarker, and a temporal pattern of the activity pattern.

5. The computer-program product of claim 1, wherein the computer-program mechanism comprises instructions for receiving additional information specifying one of: a vital sign of the second individual as a function of time, a biomarker of the second individual as a function of time, and an activity pattern of the second individual as a function of time; and
   wherein determining the need for milk is based on one of: a temporal pattern of the vital sign, a temporal pattern of the biomarker, and a temporal pattern of the activity pattern.

6. The computer-program product of claim 1, wherein determining the need for milk is based on a day of the week.

7. The computer-program product of claim 1, wherein the feedback maximizes an average volume of the milk collected during a given breast-pumping session.

8. The computer-program product of claim 1, wherein the computer-program mechanism comprises instructions for providing to the individual encouragement about the milk collection.

* * * * *